United States Patent [19]

Hilborn

[11] Patent Number: 5,435,840
[45] Date of Patent: Jul. 25, 1995

[54] BRANDING PHARMACEUTICAL DOSAGE FORMS, FOOD AND CONFECTIONERY PRODUCTS WITH AQUEOUS INGESTIBLE INKS

[75] Inventor: G. Roland Hilborn, Royersford, Pa.

[73] Assignee: Berwind Pharmaceutical Services, Inc., West Point, Pa.

[21] Appl. No.: 657,088

[22] Filed: Feb. 19, 1991

Related U.S. Application Data

[63] Continuation of Ser. No. 473,897, Feb. 2, 1990, Pat. No. 5,006,362, which is a continuation of Ser. No. 191,704, May 9, 1988, abandoned.

[51] Int. Cl.6 .......................... C09D 11/00; C08J 3/12
[52] U.S. Cl. .................. 106/20 R; 426/383; 523/100; 523/105
[58] Field of Search .............. 101/37; 106/24, 26, 106/30, 20 R; 426/383; 523/100, 105

[56] References Cited

U.S. PATENT DOCUMENTS

| | | | |
|---|---|---|---|
| 2,948,626 | 8/1960 | Sanders | 106/2 X |
| 3,149,040 | 9/1964 | Jeffries | 167/82 |
| 3,258,347 | 6/1966 | Brown | 106/30 |
| 3,297,535 | 1/1967 | Butler et al. | 167/82 |
| 3,395,202 | 7/1968 | Yen | 264/132 |
| 3,413,396 | 11/1968 | Stearns | 264/132 |
| 3,436,453 | 4/1969 | Vincent et al. | 424/6 |
| 3,475,187 | 10/1969 | Kane | 106/22 |
| 3,533,811 | 10/1970 | Clements et al. | 106/2 X |
| 3,554,767 | 1/1971 | Daum et al. | 106/162 X |
| 3,601,041 | 8/1971 | Perra et al. | 101/37 |
| 3,694,237 | 9/1972 | Piotrowski | 106/30 |
| 3,802,896 | 4/1974 | Westall et al. | 106/24 X |
| 3,860,552 | 1/1975 | Montillier | 524/853 |
| 3,950,290 | 4/1976 | Drury et al. | 427/288 X |
| 3,961,082 | 6/1976 | Winkler | 426/87 |
| 3,981,984 | 9/1976 | Signorino | 106/187 X |
| 3,990,980 | 11/1976 | Kosel | 430/114 X |
| 4,019,911 | 4/1977 | Vijayendran et al. | 106/20 X |
| 4,165,399 | 8/1979 | Germonprez | 427/264 |
| 4,456,629 | 6/1984 | Wood et al. | 427/3 |
| 4,543,370 | 9/1985 | Porter et al. | 523/100 |
| 4,548,825 | 10/1985 | Voss et al. | 426/383 |
| 4,661,367 | 4/1987 | Forse et al. | 427/3 |
| 5,006,362 | 4/1991 | Hilborn | 426/383 X |

*Primary Examiner*—Michael Lusignan
*Attorney, Agent, or Firm*—John F. A. Earley; John F. A. Earley, III

[57] ABSTRACT

A method of marking forms such as pharmaceutical tablets, capsules, confectionery and food with a water based ingestible ink comprising mixing pigments, a polymer, and optionally a plasticizer into water to form an ink dispersion, and printing the ink dispersion onto said forms to form a trademark, logo, or the like.

25 Claims, No Drawings

BRANDING PHARMACEUTICAL DOSAGE FORMS, FOOD AND CONFECTIONERY PRODUCTS WITH AQUEOUS INGESTIBLE INKS

This is a continuation of application Ser. No. 07/473,897 filed on Feb. 2, 1990, now U.S. Pat. No. 5,006,362which was a continuation of Ser. No. 07/191,704 filed May 9, 1988, now abandoned.

TECHNICAL FIELD

This invention is in the field of applying indicia to pharmaceutical dosage forms, food products and confectionery items using an ink that primarily has a water base.

BACKGROUND OF THE INVENTION

This invention is concerned with a method of marking forms such as confectionery products, food, pharmaceutical tablets, and hard and soft gelatin capsules with a water based ingestible ink.

Reference is made to James C. Brown U.S. Pat. No. 3,258,347 issued on Jun. 28, 1966 for "Edible Pharmaceutical Ink"; Roy Y. Sanders, Jr. U.S. Pat. No. 2,948,626 issued on Aug. 9, 1960 for "Edible Pharmaceutical Ink and Process of Using Same"; Chester J. Piotrowski U.S. Pat. No. 3,694,237 issued on Sep. 26, 1972 for "Edible Ink"; and Stuart C. Porter et al. U.S. Pat. No. 4,543,370 issued on Sep. 24, 1985 for "Dry Edible Film Coating Composition, Method and Coating Form". These patents are incorporated herein by reference.

Prior art ingestible inks suitable for marking forms such as confectionery products, food, pharmaceutical tablets, and hard and soft gelatin capsules have a shellac base in ethyl alcohol. One of the problems in marking such forms and one of the more important parameters for these inks is drying time. Brown U.S. Pat. No. 3,258,347, which refers to drying time as "set-to-touch-time", states that the optimum transfer characteristics of the ink are obtained when the set-to-touch-time is two to four minutes. When the drying time is too slow, as is discussed in Sanders, Jr. U.S. Pat. No. 2,948,626, a tackiness problem develops resulting in spotting or smudging of the ink. Drying time is also discussed in Piotrowski U.S. Pat. No. 3,694,237 at column 1, lines 57–72 which states: "Prior art edible inks are made with dry shellac, ethyl alcohol, plasticizers and/or detackifiers, pigments, or dyes, and solvents which give a desired drying time, say three minutes. As the ink ages, a process occurs wherein the acid groups of the shellac react with the ethyl alcohol to form an ethyl ester of the shellac. The presence of the shellac ester increases the drying time of the ink, and as the amount or percentage of ester increases, the drying time is increased, eventually to a point where the drying time is too long, causing offset, or pick-off, or transfer of the ink from one printed piece or tablet to another. Accordingly, it has been noted that the drying time of prior art inks increases with age, and this limits the shelf or storage life of the ink."

The machines presently being used to print marks onto pharmaceutical, food or confectionery products use a principle that is best described as offset gravure. An engraved cylinder picks up ink as it rotates in an ink bath. Excess ink is wiped off the engraved cylinder by a doctor blade and the ink remaining in the gravure etch of the cylinder is transferred to a rubber transfer (offset) roller which rotates with its roller surface in contact with the engraved cylinder. The ink on the transfer roller is then deposited onto the end product such as a tablet, or capsule.

The form may have been film coated, sugar coated, or not coated at all. To date, almost all inks used for this purpose have been of a shellac base in ethyl alcohol. While some shellac based inks have incorporated some water into the formula by the modification of pH, the inks remain alcohol based for the most part. Accordingly, their closed cup flash point is less than 100° F., and, therefore, they must be labeled as a hazardous flammable liquid.

SUMMARY OF THE INVENTION

A pharmaceutically or confectionery acceptable ingestible ink for use on pharmaceutical, confectionery and food forms, such as hard and soft shell gelatin capsules, tablets, candy and the like, comprises about 3 to 15 parts polymer, 5 to 30 parts pigment, 0.0 to 20.0 parts plasticizer, 0.0 to 17.0 parts alcohol, 0.0 to 0.001 parts antifoaming agent, and sufficient water to make 100 parts, by weight of the ink. A preferred ink formulation comprises about 10 parts polymer, 22 parts pigment, 7 parts HPMC (6 cps), 12 parts alcohol, 0.001 parts antifoaming agent, and sufficient water to make 100 parts, by weight, of the ink.

The polymer may be methylcellulose, hydroxypropyl methylcellulose (HPMC), hydroxypropyl cellulose (HPC), cellulose acetate phthalate, ethylcellulose, polyvinylpyrrolidone, sodium ethylcellulose sulphate, zein, polyvinylacetatephthalate, methacrylic acid-methacrylic acid ester co-polymer, or other film forming polymer used for coating tablets and the like.

Any of the pigments heretofore used in making ingestible ink may be used in the ink. Examples are discussed in Porter et al. U.S. Pat. No. 4,543,370. Examples of pigments include FD&C and D&C lakes, titanium dioxide, magnesium carbonate, talc, pyrogenic silica, iron oxides, channel black, and insoluble dyes. Also natural pigments such as riboflavin, carmine 40, curcumin, and annatto. Other examples are listed in Jeffries U.S. Pat. No. 3,149,040 and Butler et al. U.S. Pat. No. 3,297,535, as well as in Signorino U.S. Pat. No. 3,981,984, which are incorporated herein by reference.

The plasticizer may be any of the polymer plasticizers discussed in Porter et al. U.S. Pat. No. 4,543,370. Exemplary of the polymer plasticizer are polyethyleneglycol, for example, polyethylene glycol having a molecular weight of 200 to 8000 (Carbowax by Union Carbide), glycerin, propylene glycol, Triacetin (Pfizer's glycerin triacetate), acetylated monoglyceride, and Citroflex 2 (triethyl citrate), Citroflex 4 (tributyl citrate), Citroflex A2 (acetyl triethyl citrate), Citroflex A4 (acetyl tributyl citrate), diethyl phthalate, and mineral oil. Citroflex 2, 4, A2 and A4 are made by Pfizer and are plasticizers adapted for use with organic solvents.

The polymer plasticizer, to soften the polymer and make it less brittle, may be a liquid or a solid plasticizer, and a preferred plasticizer is a liquid such as polyethylene glycol 400.

Small amounts of alcohol may be used as a preservative or anti-foam agent. Examples of the alcohol that may be used are methanol, ethanol, isopropanol, and n-butanol, in amounts that are not sufficient to lower the flash point of the ink below 100° F. so as not to be classified as flammable by the Department of Transportation (DOT) of the U.S. government.

The antifoam may be Medical Anti-Foam (A-compound simethicone by Dow Corning) or dimethyl polysiloxane.

The inks made from the above formula with the water soluble polymer and with small amounts of alcohol still have a flash point above 100° F., and therefore are not classified as a hazardous flammable liquid.

With all the water present in these inks there was concern about the ability of the ink to dry on the offset gravure printing equipment used in this process of marking tablets. Two properties of the formula indicated possible problems. One is the latent heat of vaporation and the other in the set-to-touch-time.

Looking at the following Table 1 of latent heats of vaporation illustrates the problem.

TABLE 1

| MATERIAL | LATENT HEAT OF VAPORATION |
| --- | --- |
| Water | 540 Calories per gram |
| Ethanol | 204 Calories per gram |
| Methanol | 260 Calories per gram |
| Normal butanol | 141 Calories per gram |

Table 1 shows that to evaporate water requires from two to four times the amount of energy that is required to evaporate alcohol.

From Piotrowski U.S. Pat. No. 3,694,237, it is known that the ideal set-to-touch-time for a shellac-alcohol ink is two to four minutes. The set-to-touch-time for the inks disclosed in this patent application is from ten to 18 minutes.

Yet, in spite of all this evidence that teaches away from the present invention, the ink does perform very satisfactorily. The ink does not transfer from the tablet because of slow drying.

This aqueous ink adheres to problem substrates from which shellac alcohol inks rub off after drying.

One process of making the ink is a wet process in which the ink components are combined and run through dispersing mills in a liquid form.

Another process of making the ink is a dry process where the dry components are combined and run through a hammermill dry. The resulting dry material is combined with the liquid parts by mixing the dry material into the liquid in a blender. The resulting ink had the same properties as if it had been made by the wet process.

DETAILED DESCRIPTION

This invention is concerned with the composition of inks suitable for ingestion that are used to mark forms such as confectionery products, food, pharmaceutical tablets, and hard and soft gelatin capsules, including medicinal tablets, vitamin tablets, aspirin tablets, capsules, chewing gum balls, cereal, cookies, meats, fruit, pasta, and the like.

The following examples illustrate the invention with the ingredients being given in percent by weight and in grams.

EXAMPLE 1

| Ingredients | Percent by Weight | Grams |
| --- | --- | --- |
| Water | 49.00 | 2450 |
| Propylene Glycol | 10.00 | 500 |
| Methanol | 8.00 | 400 |
| Isopropanol | 4.00 | 200 |
| HPMC (6 cps) | 7.00 | 350 |

-continued

| Ingredients | Percent by Weight | Grams |
| --- | --- | --- |
| Black Iron Oxide | 22.00 | 1100 |

(a) In a wet method, the propylene glycol, HPMC and black iron oxide are mixed into the water, and the resulting mixture is run through a dispersing mill in liquid form for five minutes at room temperature until a fine dispersion is obtained.

(b) In a dry method, the propylene glycol, HPMC and black iron oxide are mixed together and then run through a hammermill dry. The resulting dry power is then mixed into the water in a blender for about fifteen minutes at room temperature until a fine dispersion is obtained.

(c) The ink of Example 1(a) is placed into a bath of an offset gravure printing machine where an engraved cylinder picks up the ink as it rotates in the bath, the excess ink is wiped off by a doctor blade, and the remaining ink on the gravure etch of the engraved cylinder is transferred to a rubber transfer (offset) roller which transfers the ink onto tablets.

(d) The ink of Example 1(b) is poured into a bath of an offset gravure printing machine when an engraved cylinder picks up the ink as it rotates in the bath, the excess ink is wiped off by a doctor blade, and the remaining ink on the gravure etch of the engraved cylinder is transferred to a rubber transfer (offset) roller which contacts and transfers the ink onto tablets.

Other examples of ink that illustrate the invention and that are made in accordance with the wet method of Example 1(a) and are applied in accordance with Example 1(c), or made as disclosed in Example 1(b) and applied as in Example 1(d), are as follows.

EXAMPLE 2

| Ingredients | Percent by Weight | Grams |
| --- | --- | --- |
| Water | 49.00 | 2450 |
| Propylene Glycol | 10.00 | 500 |
| Methanol | 8.00 | 400 |
| Isopropanol | 4.00 | 200 |
| HPMC (6 cps) | 7.00 | 350 |
| FD&C Blue Aluminum Lake | 6.90 | 345 |
| Titanium Dioxide | 15.10 | 755 |

EXAMPLE 3

| Ingredients | Percent by Weight | Grams |
| --- | --- | --- |
| Water | 49.00 | 2450 |
| Propylene Glycol | 10.00 | 500 |
| Methanol | 8.00 | 400 |
| Isopropanol | 4.00 | 200 |
| HPMC (6 cps) | 7.00 | 350 |
| FD&C Red Aluminum Lake | 19.30 | 969 |
| Titanium Dioxide | 2.70 | 135 |

EXAMPLE 4

| Ingredients | Percent by Weight | Grams |
| --- | --- | --- |
| Water | 66.10 | 859.30 |
| Methyl Alcohol | 9.50 | 123.50 |
| Black Iron Oxide | 14.00 | 182.00 |
| HPMC (15 cps) | 5.70 | 74.10 |

-continued

| Ingredients | Percent by Weight | Grams |
| --- | --- | --- |
| Isopropyl Alcohol | 4.70 | 61.10 |

EXAMPLE 5

| Ingredient | Percent by Weight | Grams |
| --- | --- | --- |
| Water | 66.00 | 924.00 |
| Methyl alcohol | 11.30 | 158.20 |
| Propylene glycol | 2.00 | 28.00 |
| Black Iron Oxide | 14.00 | 196.00 |
| HPMC (15 Cps) | 5.00 | 70.00 |
| HPMC (3 cps) | 0.70 | 9.80 |
| HPC (LF) | 1.00 | 14.00 |

EXAMPLE 6

| Ingredients | Percent by Weight | Grams |
| --- | --- | --- |
| Water | 55.00 | 770.00 |
| Methyl Alcohol | 14.00 | 196.00 |
| Propylene Glycol | 2.00 | 28.00 |
| Normal Butyl Alcohol | 3.00 | 42.00 |
| Black Iron Oxide | 14.00 | 196.00 |
| HPMC (15 cps) | 3.00 | 42.00 |
| HPMC (5 cps) | 3.00 | 42.00 |
| HPMC (3 cps) | 3.00 | 42.00 |
| (HPC) Klucel LF | 3.00 | 42.00 |

Klucel LF is the LF grade of a hydroxypropyl cellulose made by Hercules, Inc.

EXAMPLE 7

| Ingredients | Percent by Weight | Grams |
| --- | --- | --- |
| Water | 80.29 | 1846.67 |
| Black Iron Oxide | 14.00 | 322.00 |
| HPMC (15 cps) | 5.70 | 131.10 |
| Anti-foaming agent (10% solution) Medicinal Antifoam (A-compound simethicone by Dow Chemical) | 0.01 | 0.23 |

EXAMPLE 8

| Ingredients | Percent by Weight | Grams |
| --- | --- | --- |
| Water | 61.16 | 795.08 |
| HPMC (15 cps) | 5.70 | 74.10 |
| FD&C Red 40 Lake | 17.50 | 227.50 |
| Titanium Dioxide | 2.50 | 32.50 |
| Methanol | 8.79 | 114.27 |
| Isopropanol | 4.35 | 56.55 |

EXAMPLE 9

| Ingredient | Percent by Weight | Grams |
| --- | --- | --- |
| Water | 61.16 | 856.24 |
| HPMC (15 cps) | 5.70 | 79.80 |
| FD&C Blue 1 Lake | 6.21 | 89.94 |
| Titanium Dioxide | 13.79 | 193.06 |
| Methanol | 8.79 | 123.06 |
| Isopropanol | 4.35 | 60.90 |

EXAMPLE 10

| Ingredients | Percent by Weight | Grams |
| --- | --- | --- |
| Water | 61.16 | 1,039.72 |
| HPMC (15 cps) | 5.70 | 96.90 |
| Black Iron Oxide | 20.00 | 340.00 |
| Methanol | 8.79 | 149.43 |
| Isopropanol | 4.35 | 73.95 |

EXAMPLE 11

| Ingredients | Percent by Weight | Grams |
| --- | --- | --- |
| Water | 66.20 | 926.80 |
| Methanol | 9.50 | 133.00 |
| Isopropanol | 4.70 | 65.80 |
| HPMC (15 cps) | 5.70 | 79.80 |
| Titanium Dioxide | 14.00 | 196.00 |

EXAMPLE 12

| Ingredients | Percent by Weight | Grams |
| --- | --- | --- |
| SURELEASE (E-7-7050) polymeric dispersion | 84.99 | 1,104.87 |
| Black Iron Oxide (Pigment) | 15.00 | 195.00 |
| Anti-foaming agent (as in Example 7) | 0.01 | 0.13 |

The ink of example 12 is heat treated at 40° C. for one hour for the film to form completely. Also, any of the commercially available suspension polymer systems may be substituted for the SURELEASE dispersion, such as Aquacoat (from FMC corporation) and Eudragit (from Rohm Pharma GmbH, Darmstadt).

SURELEASE dispersion is a product of Colorcon, Inc., West Point, Pa., and is a polymeric dispersion comprising ethylcellulose, dibutyl sebacate, oleic acid, and fumed silica.

EXAMPLE 13

| Ingredients | Percent by Weight | Grams |
| --- | --- | --- |
| Water | 60.66 | 788.60 |
| HPMC (6 cps) | 5.70 | 74.00 |
| Propylene glycol | 0.50 | 6.48 |
| FD&C Red No. 40 Aluminum Lake | 17.50 | 227.50 |
| Titanium Dioxide | 2.50 | 32.50 |
| Methanol | 8.79 | 114.27 |
| Isopropanol | 4.35 | 56.55 |

The vehicle for the pigment is the polymer, which acts as a binder and carrier for the pigment.

The preferred quantity of polymer, such as HPMC, used in producing the ingestible inks of this invention is from about 3% to 15% by weight of the ink.

The percentage by weight of the inks of the polymer may vary due to the viscosity ranges of the polymer. For example, hydroxypropyl methylcellulose (HPMC) has common viscosity types of 3 cps, 6 cps, 15 cps and 50 cps. The higher the viscosity, the more viscous (thicker) the ink is. By weight of the ink, 7 percent by weight of the ink of 6 cps hydroxypropyl methylcellulose has been found to be advantageous.

Preferrably, the quantity of the pigment in the ink is approximately 5% to 30% by weight of the ink. Below 5%, printed ink is weak. Above 30%, the color of the printed ink is weak since a higher pigment-to-polymer ratio affects the ability of the ink to transfer properly. Preferably, the pigment-to-polymer ratio when using 6 cps hydroxypropyl methycellulose is 7 parts of the 6 cps hydroxypropyl methylcellulose to 22 parts of pigment. For different grades of hydroxypropyl methylcellulose, the pigment-to-polymer ratios differ.

The plasticizer softens the polymer and makes it less brittle. The plasticizer also modifies the drying rate.

I have also found that my inks may be made without adding the customary plasticizers, propylene glycol or polyethylene glycol; the water in the system may act as a plasticizer.

Alcohol may be used in my ink to modify the drying rate, to help reduce foaming, to help preserve the ink, and to increase the wetability of the ink or reduce the surface tension. Above 17% by weight of the ink, the alcohol causes the ink to have a closed cup flash point below 100 degrees Farenheit, thus requiring the ink to be labeled as a hazardous flamable liquid as defined by the Department of Transportation. Methanol, ethanol, isopropynol and n-butanol are the only alcohols approved for use by the Food and Drug Administration.

In addition to alcohol, other preservatives may be used, such as sodium benzoate.

The anti-foaming agent reduces foaming while the ink is on the printing machine. The Food and Drug Administration limits the use of anti-foaming agents above 0.001% by weight of the finished ink. In addition to Medicinal Antifoam (A-compound simethicone by Dow Corning) and dimethyl polysiloxane, any acceptable food grade anti-foamer may be used in the ink, if needed.

When making the ink, a wet process may be used, such as the method used to make shellac type ink, disclosed in Brown U.S. Pat. No. 3,258,347.

Another process of making the ink is a dry process where the dry components are combined and run through a hammermill dry. The resulting dry material is combined with the liquid parts by mixing the dry material into the liquid in a blender. Previous shellac inks have not been made dry since the shellac could soften and prevent it from getting through the hammermill.

ADVANTAGES

Performance of this aqueous ink is equal to and sometimes superior to the performance of shellac based alcohol inks. Moreover, it is easier to clean this aqueous ink from the printing machine because, unlike shellac based alcohol inks which require cleaning by alcohol solvents or by highly caustic solutions, only water is needed to clean-up my inventive water-based inks from the printing machines. Accordingly, operator exposure to alcohol cleaning solvents and their fumes is greatly reduced.

The inventive inks are not flammable at below 100° F. and are therefore shipped more easily.

The wet and dry components of my ink may be kept separate from one another until ink is needed, and this extends the shelf life of the ink. Further, the settling out problem associated with prior art liquid ink suspensions is eliminated.

Inks made with the shellac alcohol system that uses aluminum lakes for pigments sometimes gel in a short period of time (less than a week). This is probably due to a reaction between the shellac and the aluminum. Inks produced in my water based system have not exhibited this disadvantage.

I claim:

1. An ink composition for dispersal into water to form a water based ingestible ink for marking forms such as pharmaceutical tablets, capsules, confectioneries, or food using an offset gravure printing machine, comprising a dry mixture of 3 to 15 parts polymer, 0 to 14 parts plasticizer, and 5 to 30 parts pigment, said dry mixture to be dispersed with a sufficient amount of water to make 100 parts to form the water based ingestible ink for marking forms using an offset gravure printing machine, said dry mixture having a ratio of polymer to pigment on a weight to weight basis, said ratio being about equal to or less than 1 part polymer for each part pigment.

2. An ink composition for dispersal into water to form a water based ingestible ink for marking forms such as pharmaceutical tablets, capsules, confectioneries, or food using an offset gravure printing machine, comprising a dry mixture of 3 to 15 parts polymer, 0 to 14 parts plasticizer, and 5 to 30 parts pigment, said dry mixture to be dispersed with a sufficient amount of water to make 100 parts to form the water based ingestible ink for marking forms using an offset gravure printing machine, said dry mixture having an amount of polymer about equal to or less than the amount of pigment in the dry mixture on a weight to weight basis.

3. The ink composition of claim 2,
the polymer being methylcellulose, hydroxypropyl methycellulose, hydroxypropyl cellulose, cellulose acetate phthalate, ethylcellulose, polyvinylpyrrolidone, sodium ethylcellulose sulphate, zein, polyvinylacetatephthalate, or methacrylic acid-methacrylic acid ester co-polymer.

4. The ink composition of claim 2,
the plasticizer being polyethylene glycol having a molecular weight in the range of 200 to 8000, glycerin, propylene glycol, glycerinetriacetate, acetylated monoglyceride, triethyl citrate, tributyl citrate, acetyl triethyl citrate, acetyl tributyl citrate, or diethyl phthalate.

5. The ink composition of claim 2,
the plasticizer being polyethylene glycol 400.

6. The ink composition of claim 2,
the plasticizer being a liquid plasticizer.

7. The ink composition of claim 2,
the pigment being FD&C and D&C lakes, titanium dioxide, magnesium carbonate, talc, pyrogenic silica, iron oxides, channel black, riboflavin, carmine 40, curcumin, annatto, or insoluble dyes.

8. The ink composition of claim 2,
the plasticizer being greater than 0 parts to 14 parts.

9. A water-based ingestible ink for marking forms such as pharmaceutical tablets, capsules, confectioneries, or food using an offset gravure printing machine, comprising
3 to 15% by weight of a polymer,
0 to 14% by weight of a plasticizer,
5 to 30% by weight of a pigment, and water,
said ink having a closed cup flash point equal to or above 100° F.

10. The water-based ingestible ink of claim 9,
the polymer being methylcellulose, hydroxypropyl methycellulose, hydroxypropyl cellulose, cellulose acetate phthalate, ethylcellulose, polyvinylpyrrolidone, sodium ethylcellulose sulphate, zein, polyvinylacetatephthalate, or methacrylic acidmethacrylic acid ester co-polymer.

11. The water-based ingestible ink of claim 9, the plasticizer being polyethylene glycol having a molecular weight in the range of 200 to 8000, glycerin, propylene glycol, glycerinetriacetate, acetylated monoglyceride, triethyl citrate, tributyl citrate, acetyl triethyl citrate, acetyl tributyl citrate, or diethyl phthalate.

12. The water-based ingestible ink of claim 9, the plasticizer being polyethylene glycol 400.

13. The water-based ingestible ink of claim 9, the plasticizer being a liquid plasticizer.

14. The water-based ingestible ink of claim 9, the pigment being FD&C and D&C lakes, titanium dioxide, magnesium carbonate, talc, pyrogenic silica, iron oxides, channel black, riboflavin, carmine 40, curcumin, annatto, or insoluble dyes.

15. The water-based ingestible ink of claim 9, further including
an alcohol in sufficient amount to act as a preservative and anti-foaming agent but insufficient in amount to lower the flash point below 100° F.

16. The water-based ingestible ink of claim 15, the alcohol being methanol, ethanol, isopropanol, or n-butanol.

17. The water-based ingestible ink of claim 15, the alcohol being about 0 to 17% by weight of the ink.

18. The water-based ingestible ink of claim 9, further including
an anti-foaming agent.

19. The water-based ingestible ink of claim 18, the anti-foaming agent being A-compound simathicone or dimethyl polysiloxane.

20. The water-based ingestible ink of claim 18, the anti-foaming agent being A-compound simathicone from about 0 to 0.001% by weight of the ink.

21. The ink of claim 9, said ink having a set-to-touch time ranging from 10 to 18 minutes.

22. The ink of claim 9, the polymer, the plasticizer and the pigment being safely ingestible.

23. The ink of claim 9, the ink consisting essentially of the polymer, the plasticizer, the pigment and water.

24. The ink of claim 9, a range x of the plasticizer being $0 < X \leq 14\%$.

25. A water-based ingestible ink for marking forms such as pharmaceutical tablets, capsules, confectioneries, or food using an offset gravure printing machine, comprising
3 to 15% by weight of a polymer,
0 to 14% by weight of a plasticizer,
5 to 30% by weight of a pigment, and water,
said ink having a closed cup flash point equal to or above 100° F.,
the polymer being methylcellulose, hydroxypropyl methycellulose, hydroxypropyl cellulose, cellulose acetate phthalate, ethylcellulose, polyvinylpyrrolidone, sodium ethylcellulose sulphate, zein, polyvinylacetatephthalate, or methacrylic acid-methacrylic acid ester co-polymer,
the plasticizer being polyethylene glycol having a molecular weight in the range of 200 to 8000, glycerin, propylene glycol, glycerinetriacetate, acetylated monoglyceride, triethyl citrate, tributyl citrate, acetyl triethyl citrate, acetyl tributyl citrate, or diethyl phthalate, and
the pigment being FD&C and D&C lakes, titanium dioxide, magnesium carbonate, talc, pyrogenic silica, iron oxides, channel black, riboflavin, carmine 40, curcumin, annatto, or insoluble dyes,
and further including
an alcohol in sufficient amount to act as a preservative and anti-foaming agent but insufficient in amount to lower the flash point below 100° F.,
the alcohol being methanol, ethanol, isopropanol, or n-butanol,
the alcohol being about 0 to 17% by weight of the ink, and
an anti-foaming agent,
the anti-foaming agent being A-compound simathicone from about 0 to 0.001% by weight of the ink.

* * * * *